United States Patent [19]

Herzog

[11] Patent Number: 5,380,764

[45] Date of Patent: Jan. 10, 1995

[54] COMPOSITION OF VITAMIN A, GLUCOSE AND HYDROGEN PEROXIDE FOR COSMETIC OR PHARMACEUTICAL USE

[76] Inventor: Paul Herzog, 37-39, route du Monteliza, Saint-Legier, Switzerland, 1806

[21] Appl. No.: 10,513

[22] Filed: Jan. 28, 1993

Related U.S. Application Data

[63] Continuation-in-part of Ser. No. 630,690, Dec. 20, 1990, abandoned, which is a continuation of Ser. No. 363,563, Jun. 8, 1989, abandoned.

[30] Foreign Application Priority Data

Dec. 21, 1989 [CH] Switzerland ............... 4582/89

[51] Int. Cl.$^6$ ............................................. A61K 31/07
[52] U.S. Cl. ................................... 514/725; 514/458; 514/859; 514/23; 514/25
[58] Field of Search ............... 514/725, 458, 859

[56] References Cited

U.S. PATENT DOCUMENTS

| | | | |
|---|---|---|---|
| 3,729,568 | 4/1973 | Kligman | 424/318 |
| 3,954,974 | 5/1976 | Herzog et al. | 424/130 |
| 4,163,800 | 8/1979 | Wickett et al. | 424/326 |
| 4,333,924 | 6/1982 | Bowley et al. | 424/170 |
| 4,485,091 | 11/1984 | Fitton | 424/62 |
| 4,534,979 | 8/1985 | Loev et al. | 514/529 |
| 4,826,681 | 5/1989 | Jacquet et al. | 424/613 |
| 4,826,828 | 5/1989 | Wilmott et al. | 514/63 |
| 4,847,078 | 7/1989 | Sheppard et al. | 424/80 |
| 4,876,381 | 10/1989 | Lang et al. | 560/56 |

OTHER PUBLICATIONS

Chemical Abstracts, vol. 110 (1989) No. 82264r (Counts et al).
Chemical Abstracts 71:53475f, 1969 (Zabova et al).
Chemical Abstracts 97:203100h, 1982 (Sekimoto et al).
Chemical Abstracts 99:218589q, 1983 (Sekimoto et al).

*Primary Examiner*—Marianne M. Cintins
*Assistant Examiner*—T. J. Criares

[57] ABSTRACT

A composition for use as a cosmetic or pharmaceutical consisting essentially of Vitamin A or ester, glucose in an amount of between about 0.5 and $10°/_{oo}$ by weight and a stable aqueous emulsion of hydrogen peroxide.

18 Claims, No Drawings

COMPOSITION OF VITAMIN A, GLUCOSE AND HYDROGEN PEROXIDE FOR COSMETIC OR PHARMACEUTICAL USE

This is a continuation-in-part of application Ser. No. 07/630,690, filed Dec. 20, 1990, now abandoned, which is a continuation of application No. 07/363,563 filed Jun. 8, 1989, now abandoned.

BACKGROUND OF THE INVENTION

The therapeutic action of vitamin A in its acid (retinoic acid), aldehyde (retinal) or alcohol form (retinol) is well known in dermatology.

The use of a composition including both an ester of vitamin A and a stable emulsion of hydrogen peroxide was proposed in patent CH-A-670 951. Such an emulsion has a particularly high capacity for releasing oxygen (paraosmotic pressure of about 10 atm), the effect of which is in particular to increase the movement of the vitamin A derivative across the outer layers of the skin, where the conversion of the vitamin A ester into retinoic acid may proceed.

Katzberg has reported in Anat. Rec. 112, 418 (1952) and later H. Pinkus in Dermatologica, 106, 28 (1953), that the life span of a human epidermal cell is of 101 days during the ten first years of life and decreases subsequently to 46 days at the age of 80. This means that time causes an ageing which is evidenced by a decreased capacity of the cells to regenerate the epidermis. When the energy which can be used physiologically by the cells is no longer sufficient, for instance because of an inadequate permeability of the capillaries or because of an inadequate capillary circulation, there is then an increase in the disappearance rate of the cells, which is accompanied by a significant impairment of their vital functions.

Whilst multiplication and growth of epidermal somatic cells require oxygen, the survival of cells is dependent upon glycolysis, which is an oxidative breakdown of glucose. Actually, to keep its structure ready to function or to fulfil its functions, each individual cell of the body needs a large amount of energy.

Should the energy, or a part of the energy needed to keep the cell functioning, not be available, damages may occur which are reversible at the beginning, but which may lead to a loss of cell structure and eventually to premature death, if not treated.

Up to now, no composition was available for cosmetic or for pharmaceutical use, which would associate the effects of vitamin A and of hydrogen peroxide and which could also supply the cell with the energy it needs.

The new composition according to the invention supplies this energy and, accordingly, is capable of restoring immediately the proper functioning of each individual cell, when the capillary insufficiency is due to an inadequate energy supply, which is particularly beneficial for cutaneous tissues.

THE INVENTION

Specifically, the object of the invention is a composition for cosmetic or for pharmaceutical use containing vitamin A in the form of an ester, or as the acid and glucose, in association with a stable aqueous emulsion of hydrogen peroxide.

PREFERRED EMBODIMENTS OF THE INVENTION

The energy is generated through the oxidative breakdown of glucose, which is made possible due to an adequate oxygen supply from hydrogen peroxide.

Glucose is transported through the outer layers of the skin with vitamin A (ester or free acid) under the effect of the pressure exerted by nascent oxygen. The energy released through glycolysis can then be used under the skin.

Under in vivo conditions, the oxidative breakdown of 1 mole of glucose ($C_6H_{12}O_6 + 6O_2 = 6CO_2 + 6H_2O$) results in the production of 690 kcal and is associated with the formation of 38 moles of adenosine triphosphate (ATP).

Specifically, glycolysis is the oxidative breakdown of glucose in a living organism under the effect of enzymes. ATP is an energy-rich phosphate donor in numerous phosphorylation reactions and also plays a role in the synthesis of ribonucleic acids.

The compositions of the invention do not require the addition of glucose, although the inclusion of this component is advantageous for the reasons given above. However, the present compositions include the combination of vitamin A or one of its derivatives and a hydrogen peroxide emulsion.

The application of the composition according to the invention, for example as a cream, ensures that a rapid breakdown of ATP to adenosine diphosphate (ADP) is maintained in the cutaneous tissues in in contact with said composition, whereby the energy necessary for the metabolism of the cell is released: for example, for the synthesis of collagen, which is an important factor for preserving in particular the elasticity of the derm.

The compositions of the invention become fully effective right after being applied to the skin with the pressure of the oxygen and water becoming released from the decomposition of the peroxide. Thus, vitamin A, oxygen and water penetrate into the subcutaneous tissue and become available to the cells. The following reactions can then take place:

1) Saponification of vitamin A palmitate (RETINOL)
$$(R1)-CH_2O-CO-(R2) + H_2O \longrightarrow \underset{\text{Retinol}}{(R1)-CH_2OH} + \underset{\text{Palmitic acid}}{(R2)-COOH}$$

2) Oxidation to aldehyde (RETINAL)
$$(R1)-CH_2OH + 1/2\ O_2 \longrightarrow \underset{\text{Retinal}}{(R1)-CHO} + H_2O$$

3) Oxidation of the aldehyde to retinoic acid
$$\underset{\text{Retinal}}{(R1)-CHO} + 1/2\ O_2 \longrightarrow \underset{\text{Retinoic acid}}{(R1)-COOH}$$

The latter compound (Vitamin A in its acid form) being thus involved in the cellular metabolism. It is thus noted that sufficient oxygen and water is released from the emulsion to enable these reactions to take place.

Concerning retinoic acid, which can be used as such in the composition of the invention, the pressure of native oxygen on the surface of the skin drastically accelerates its passage through the skin and significantly decreases possible side effects when used externally. The oxidation mechanism does not occur as the compound is metabolized as would occur in the sub-cutaneous tissue.

This shows how unique is the combination of the invention either in terms of ingredients or activity. As a cosmetic, it has been proved that such a combination is particularly useful for combating premature aging of the skin.

Vitamin A in its acid form is conventionally used for the treatment of acne, but is a fairly aggressive material which can cause sensitization of skin when utilized in relatively high concentrations. While some amounts of Vitamin A when used alone may penetrate the skin, this occurs to the detriment of the outer layers, which may be sensitized as noted above.

Hydrogen peroxide itself is a strong disinfectant that can cause rapid oxidation of the skin. It has not been utilized in any skin conditioning formulations for that reason. It has, of course, been used in disinfecting solutions, and the present inventor discovered how to ameliorate its effects by stabilizing it in an emulsion, as disclosed in U.S. Pat. No. 3,954,974. This patent does not disclose that such emulsions have utility in skin creams for cosmetic or pharmaceutical compositions.

Glucose has been utilized in topical cosmetics in small amounts as an antioxidant. There is no disclosure that glucose can be added to such compositions for transport through the outer layers of the skin for decomposition to provide energy to the cells therein.

The advantageous effects on the skin are obtained through the use of the present compositions, because the action of the peroxide on the skin is controlled by its incorporation and stabilization in the emulsion. Moreover, its decomposition provides oxygen which drives the Vitamin A and glucose beneath the outer layer of the skin. Once therein, the oxygen reacts with Vitamin A as noted above to produce retinoic acid. The cellular fluids include some glucose which can decompose to provide energy to this reaction, but the intentional addition of glucose to the composition provides additional energy to facilitate this reaction. The supply of retinoic acid to the cells, in turn, provides beneficial effects on the skin.

The hydrogen peroxide emulsions, which can be used within the scope of the present invention, can be either of the water-in-oil, or oil-in-water type.

A stable oil-in-water emulsion of hydrogen peroxide particularly well suited for preparing a composition according to the invention is described in U.S. Pat. No. 3,954,974.

Since no toxic by-products are formed during the breakdown of hydrogen peroxide, such emulsions can include a high concentration of nascent oxygen which reinforces all the more the action of vitamin A, while at the same time ensuring a release of energy as a result of its reaction with glucose.

Amongst the esters of vitamin A which can be used, one can preferably choose an ester of a fatty acid, such as the palmitate of vitamin A, or equally its acetate. Such products are sold commercially under an appropriate form; the fatty acid esters of vitamin A have the further advantage of being well tolerated by the skin and the organism.

The relative concentrations of the ester of vitamin A or of the acid, and of glucose can vary considerably, depending upon the effects which are sought. The derivative of vitamin A can be advantageously used at a concentration ranging from 1,000 to 10,000 international units (IU: expressed as vitamin A) per gram of the composition according to the invention.

As to the glucose, it is suitably included into the composition in an adequate molar proportion capable of producing through glycolysis, the amount of energy required for the cell metabolism. Preferably, one can use glucose in an amount ranging from 0.5 to $10^\circ/_{oo}$ in weight, based on the weight of the composition.

The concentrations of hydrogen peroxide in the composition obviously vary according to the oxygenating effect which is sought. In the case of a composition for cosmetic use, hydrogen peroxide is used in an amount ranging from 0.5 to 4% in weight (expressed as 100% $H_2O_2$) and in the case of a composition for pharmaceutical use, from 0.1 to 6% in weight or more depending on circumstances, based on the weight of the total composition.

Due to the well balanced nature of the emulsion composition, the excess oxygen generated not only produces an immediate oxidative breakdown of glucose, but further ensures that the palmitate or the acetate of vitamin A are converted into retinoic acid and that the extracellular medium is enriched with oxygen and water, these two products resulting from the breakdown of hydrogen peroxide.

Of course, the compositions according to the invention, can also contain the usual stabilizers, thickeners, perfumes or colouring agents. They can also contain additional active components, for example other vitamins and vitamine derivatives such as vitamin E, or liposomes.

Being based on an aqueous emulsion with a high oxygenating capacity, the compositions according to the invention further display highly advantageous disinfecting and cicatrizing properties, which are useful for treating burns, open wounds such as ulcers or complications arising from hemorrhoids.

The following examples are given for the purpose of illustrating the invention in more detail. These examples are in no way intended to be limiting.

EXAMPLE 1—A COSMETIC COMPOSITION

A first phase of the "oil" type is prepared by mixing together the following components:

| | |
|---|---|
| Petrolatum | 450 g |
| Liquid paraffin | 325 g |
| Cetyl alcohol | 160 g |
| Stearyl alcohol | 160 g |
| Monostearin | 310 g |
| Total | 1405 g |

The following components are mixed together separately, to prepare a "water" type phase:

| | | |
|---|---|---|
| $H_2O_2$, 30% | 400 g | = 0.353 moles/kg of cream |
| "Tween 80" | 125 g | |
| Salicylic acid | 9 g | |
| Vitamin A palmitate* | 63 g | |
| D,L-α-tocopherol acetate | 200 g | |
| Glucose | 18 g | = 0.01 moles/kg of cream |

| | |
|---|---|
| Distilled water | 7780 g |
| Total | 8595 g |

*1.7 million IU/g

The "oil" and the "water" phases thus prepared are then mixed together in an appropriate apparatus at a temperature comprised between 70° and 80° C., until a homogeneous emulsion is achieved. 10 kg of cream for cosmetic use are thus obtained, which contain 1.1% active oxygen, 0.01 moles/kg of glucose and 10,000 IU of vitamin A palmitate/g of cream.

EXAMPLE 2—A COSMETIC COMPOSITION

A first phase of the "oil" type is prepared by mixing together the following components:

| | |
|---|---|
| Petrolatum | 450 g |
| Liquid paraffin | 325 g |
| Cetyl alcohol | 160 g |
| Stearyl alcohol | 160 g |
| Monostearin | 310 g |
| Vitamin A palmitate* | 63 g |
| D,L-α-tocopherol acetate | 200 g |
| Total | 1668 g |

The following components are mixed together separately, to prepare a "water" type phase:

| | |
|---|---|
| $H_2O_2$, 30% | 1167 g = 1.03 moles/kg of cream |
| "Tween 80" | 125 g |
| Salicylic acid | 9 g |
| Glucose | 18 g = 0.01 moles/kg of cream |
| Distilled water | 7013 g |
| Total | 8332 g |

The "oil" and the "water" phases thus prepared are then mixed together in an appropriate apparatus at a temperature comprised between 70° and 80° C., until a homogeneous emulsion is achieved. 10 kg of cream for cosmetic use are thus obtained, which contain 3.5% active oxygen, 0.01 moles/kg of glucose and 10,000 IU of vitamin A palmitate/g of cream.

EXAMPLE 3—A PHARMACEUTICAL COMPOSITION

A first phase of the "oil" type is prepared by mixing together the following components:

| | |
|---|---|
| Petrolatum | 475 g |
| Liquid paraffin | 350 g |
| Cetyl alcohol | 175 g |
| Stearyl alcohol | 175 g |
| Monostearin | 350 g |
| D,L-α-tocopherol (vit. E) | 250 g |
| Total | 1775 g |

The following components are mixed together separately, to prepare a "water" type phase:

| | |
|---|---|
| $H_2O_2$, 30% | 1176 g |
| "Tween 80" | 150 g |
| Salicylic acid | 11 g |
| Glucose | 18 g |
| Retinoic acid "Trétinoïne" | 5 g |

| | |
|---|---|
| Distilled water | 6865 g |
| Total | 8225 g |

The "oil" and the "water" phases thus prepared are then mixed together in an appropriate apparatus at a temperature comprised between 70° and 80° C., until a homogeneous emulsion is achieved. 10 kg of cream for pharmaceutical use are thus obtained, which contain 3.5% active oxygen (hydrogen peroxide), 0.01 moles/kg of glucose and 0.05% of retinoic acid (Trétinoïne).

These compositions are perfectly well suited for numerous cosmetic or pharmaceutical uses and they proved to be particularly effective in cosmetic applications for preventing skin ageing. They can also be used for the treatment of benign disorders of the skin, such as acne. Further, these compositions have a disinfecting effect.

What I claim is:

1. A composition for use as a cosmetic or pharmaceutical consisting essentially of (1) Vitamin A in the form of an ester or as the free acid in an amount sufficient to provide an effective quantity of retinoic acid to skin cells and (2) glucose in an amount of between about 0.5 and $10°/_{oo}$ by weight and in association with (3) a stable aqueous emulsion of hydrogen peroxide, wherein the hydrogen peroxide is present in an amount of about 0.1% to about 10% by weight to supply water and oxygen to transport the Vitamin A and glucose through the outer layers of skin and to react with the Vitamin A so that the Vitamin A can provide retinoic acid to cells therein, and the glucose is present to provide energy to the reaction.

2. A composition for use as a cosmetic or pharmaceutical consisting essentially of (1) Vitamin A in the form of an ester or as the free acid in an amount ranging from about 1,000 to 10,000 IU/g of the composition to provide an effective quantity of retinoic acid to skin cells and (2) glucose in association with (3) a stable aqueous emulsion of hydrogen peroxide, wherein the hydrogen peroxide is present in an amount of about 0.1 to 10 percent by weight to supply water and oxygen to transport the Vitamin A and glucose through the outer layers of skin and to react with the Vitamin A so that the Vitamin A can provide retinoic acid to cells therein, and the glucose is present in an amount of about 0.5 to $10°/_{oo}$ by weight to provide energy to the reaction.

3. A composition for treatment of the skin, said composition consisting essentially of, as an active ingredient, Vitamin A in a form selected from the group consisting of an acetate and a palmitate, in an amount of between about 1,000 to 10,000 IU/g of the composition in combination with a substantially stable aqueous emulsion of hydrogen peroxide, wherein said emulsion comprises hydrogen peroxide in an amount of from about 0.1% up to about 4% by weight, measured as 100% peroxide, and wherein glucose is included in the composition in an amount of less than about $10°/_{oo}$ by weight.

4. A composition according to one of claims 1 or 2, characterized in that the stable aqueous emulsion of hydrogen peroxide is an emulsion of the oil-in-water type.

5. A composition for cosmetic use according to one of claims 1 or 2, characterized in that it contains from 0.5 to 4% in weight of hydrogen peroxide, based on the weight of the composition.

6. A composition according to claim 1 or 2 characterized in that the ester of vitamin A is the palmitate or acetate salt.

7. A composition for treatment of the skin, said composition consisting essentially of, as an active ingredient, Vitamin A in an amount sufficient to provide an effective quantity of retinoic acid to skin cells in combination with a substantially stable aqueous emulsion of hydrogen peroxide, wherein said emulsion comprises hydrogen peroxide in an amount of about 0.1% up to about 4% by weight, measured as 100% peroxide, and wherein glucose is included in the composition in an amount of less than about $10°/_{oo}$ by weight.

8. The composition of claim 7 wherein said vitamin A is in the form of an acid.

9. The composition of claim 7 wherein said vitamin A is in the form of vitamin A acetate.

10. The composition of claim 7 wherein said vitamin A is in the form of vitamin A palmitate.

11. The composition of claim 7 wherein the hydrogen peroxide emulsion is an oil-in-water emulsion.

12. The composition of claim 7 wherein said hydrogen peroxide concentration is about 1.2% by weight.

13. A composition for treatment of the skin, said composition consisting essentially of, as an active ingredient, Vitamin A in an amount of between about 1,000 and 10,000 IU/g of the composition to provide an effective quantity of retinoic acid to skin cells in combination with a substantially stable aqueous emulsion of hydrogen peroxide, wherein said emulsion comprises hydrogen peroxide in an amount of from about 0.1% up to about 6% by weight, measured as 100% peroxide, wherein glucose is included in the composition in an amount of less than about $10°/_{oo}$ by weight.

14. The composition of claim 13 wherein said vitamin A is in the form of an acid.

15. The composition of claim 13 wherein said vitamin A is in the form of vitamin A acetate.

16. The composition of claim 13 wherein said vitamin A is in the form of vitamin A palmitate.

17. The composition of claim 13 wherein the hydrogen peroxide emulsion is an oil-in-water emulsion.

18. A process for combatting a loss of elasticity of the skin by treating the skin with an effective amount of the composition set forth in any one of claims 7-2, wherein a sufficient amount of the Vitamin A and glucose are transported through the outer layers of the skin, thus allowing vitamin A to provide retinoic acid to cells therein, while supplying energy to the cells by decomposing the glucose.

* * * * *